United States Patent
Rabinovich et al.

(10) Patent No.: US 10,607,729 B2
(45) Date of Patent: Mar. 31, 2020

(54) SYSTEM AND METHOD FOR AUTOMATED GENERATION OF A SECURE MESSAGE

(71) Applicant: Internet Brands, Inc., El Segundo, CA (US)

(72) Inventors: Dimitri Rabinovich, Freeland, WA (US); Ahmed Morsy, Burbank, CA (US)

(73) Assignee: MH Sub I, LLC, El Segundo, CA (US)

( * ) Notice: Subject to any disclaimer, the term of this patent is extended or adjusted under 35 U.S.C. 154(b) by 1028 days.

(21) Appl. No.: 15/083,144

(22) Filed: Mar. 28, 2016

(65) Prior Publication Data
US 2017/0277833 A1    Sep. 28, 2017

(51) Int. Cl.
| | |
|---|---|
| *G06F 19/00* | (2018.01) |
| *H04L 29/06* | (2006.01) |
| *G06F 21/31* | (2013.01) |
| *G06F 21/60* | (2013.01) |
| *G06F 21/62* | (2013.01) |
| *G16H 10/60* | (2018.01) |

(52) U.S. Cl.
CPC .......... *G16H 10/60* (2018.01); *G06F 21/31* (2013.01); *G06F 21/606* (2013.01); *G06F 21/6263* (2013.01); *H04L 63/0428* (2013.01); *H04L 63/08* (2013.01)

(58) Field of Classification Search
CPC ..... G16H 10/60; H04L 63/0428; H04L 63/08; H04L 29/06; G06F 19/00; G06F 21/606; G06F 21/31; G06F 21/6263; G06F 21/60; G06F 21/62

USPC ...................... 705/3; 713/170, 165, 167, 181
See application file for complete search history.

(56) References Cited

U.S. PATENT DOCUMENTS

| | | | | |
|---|---|---|---|---|
| 2004/0078228 | A1* | 4/2004 | Fitzgerald | G06F 19/324 705/2 |
| 2005/0273365 | A1* | 12/2005 | Baumgartner | G06F 19/321 705/3 |
| 2006/0020622 | A1* | 1/2006 | Shelton | G06F 21/6245 |
| 2015/0193584 | A1* | 7/2015 | Laws | G06F 19/3418 705/3 |

* cited by examiner

Primary Examiner — Kevin Bechtel
Assistant Examiner — Quazi Farooqui
(74) Attorney, Agent, or Firm — Rutan & Tucker, LLP

(57) ABSTRACT

A non-transitory storage medium having stored thereon instructions, the instructions being executable by one or more processors to perform operations including: uploading a first data from a first extractor on a first data source and a second data from a second extractor on a second data source, parsing the first data and the second data to detect one or more patterns within one or more of the first data or the second data, responsive to detecting one or more patterns, automatically selecting a message template corresponding to the one or more detected patterns, populating the selected message template with one or more elements from one or more of the parsed first data or the parsed second data to generate a secure message, the one or more elements corresponding to the one or more detected patterns, and storing the secure message in a secure message exchange module is shown.

16 Claims, 7 Drawing Sheets

SYSTEM AND METHOD FOR AUTOMATED GENERATION OF A SECURE MESSAGE

FIELD

Embodiments of the disclosure relate to the field of secure messaging over a network. More specifically, one embodiment of the disclosure relates to a system for automatically retrieving medical data from a medical provider, generating a secure electronic message based on the retrieved medical data, storing the secure electronic message on a secure storage device, notifying a recipient of the presence the secure electronic message, and providing the recipient access to the secure electronic message within a secure portal upon authenticating the recipient.

GENERAL BACKGROUND

Today, security is at the forefront of Internet users' concerns. As stores, banks, credit card companies, health care providers, etc., have turned to the Internet for providing consumers or clients access to services and products, more personal information is being exchanged, stored and accessed over the Internet than ever before. Specifically, the healthcare field is beginning to transition to providing patients access to medical information, or communicating with patients regarding medical information, over the Internet. Some healthcare providers use electronic mail ("email") as a means of communication. However, such a means is unsecure and may not meet all privacy requirements, such as state and federal requirements, e.g., those imposed by the Health Insurance Portability and Accountability Act of 1996 (HIPAA).

For example, HIPAA Title II instructs the U.S. Dept. of Health and Human Services to create national standards for processing electronic healthcare transactions. Additionally, "secure" electronic access to health data is required by HIPAA in order for healthcare providers to remain in compliance with privacy regulations set by the U.S. Dept. of Health and Human Services. Briefly, HIPAA Title II includes the following standards and rules: National Provider Identifier Standard; Transactions and Code Sets Standards; HIPAA Privacy Rule; and HIPAA Security Rule. Specifically, the HIPAA Security Rule sets national standards for securing patients data that is stored or transferred electronically. Thus, in order to provide personal health information via electronic transmission and maintain compliance with at least HIPAA, a system having a secure method of receiving personal health information from one or more healthcare providers and a secure method of providing the personal health information to the corresponding patient is needed.

Additionally, healthcare providers often correspond with patients using similar text (e.g., similar text may be used in letters corresponding to office visits, upcoming appointments, referrals, etc.). Thus, healthcare providers continually waste time by repeatedly creating the same messages.

BRIEF DESCRIPTION OF THE DRAWINGS

Embodiments of the disclosure are illustrated by way of example and not by way of limitation in the figures of the accompanying drawings, in which like references indicate similar elements and in which.

DETAILED DESCRIPTION

Figure 1:
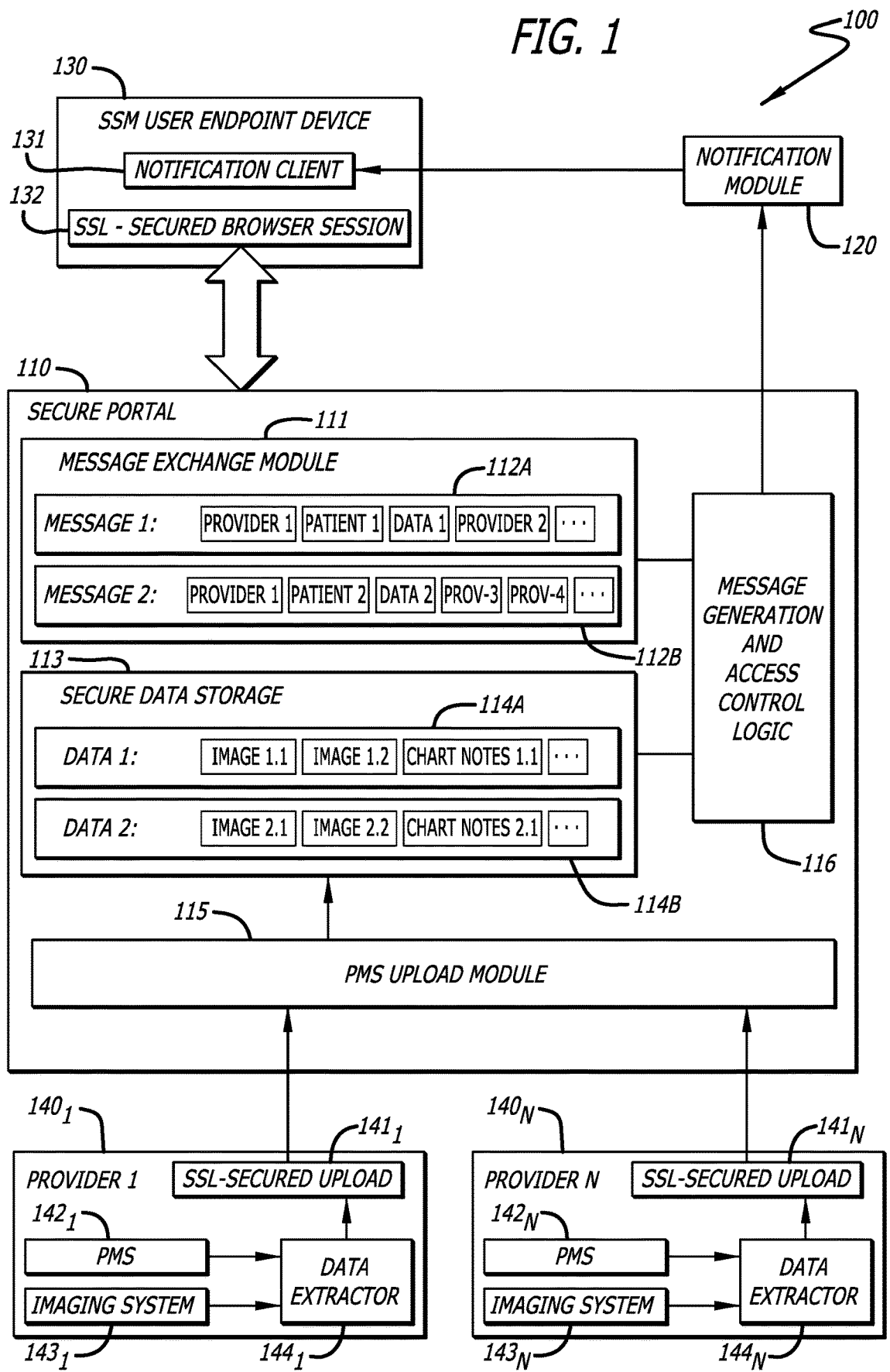
FIG. 1 is an exemplary block diagram of a Sesame Secure Messaging system.

Sesame Secure Messaging (SSM) provides a way for providers to collaborate on shared data sets containing privileged healthcare information in a more intelligent way. This system exposes only the data necessary for case management for specific patients. SSM strikes a balance between the convenience of automated record sharing and the security of message-based collaboration by utilizing smart business rules that determine when and what information should be shared. Additionally, SSM provides a way for healthcare providers to leverage their practice management software (PMS) data seamlessly for recipient data (patient and provider), imaging and clinical records and time saving messaging templates. Whereas other messaging systems treat the data being exchanged as simply transferable containers, SSM uses the data to determine the timing and content of messages.

In one embodiment, the Sesame Secure Messaging system may comprise a secure portal, one or more practice management software (PMS) systems and a notification module, wherein the secure portal and the notification module interface with one or more providers (e.g., healthcare providers) and a user endpoint device. The secure portal includes a message exchange module, a secure data storage, a PMS upload module, and a message generation and access control logic. The message exchange module may comprise a platform for storing secure messages that may be automatically generated based on parsed data that has been uploaded from one or more data sources associated with one or more healthcare providers. The message exchange module may include persistent storage that is segmented by patient wherein one or more messages may be stored and accessed in a single patient segment. Access may be provided to the corresponding patient, e.g., after providing authenticating credentials, and similarly to one or more healthcare providers. The secure portal may interface (e.g., transmit or receive a message) with the user endpoint device (e.g., of a patient) via a secure communication channel (e.g., a Secure Sockets Layer (SSL)-secured browser session) in order to provide access to one or more secure messages stored on the message exchange module. In one embodiment, the secure portal may transmit a notification to the patient endpoint device alerting the patient that a secure message has been stored for retrieval on the message exchange module, wherein the notification contains no personal health information and is transmitted via an unsecured communication channel, such as email or short message service (SMS). However, prior to providing access to a secure message on the message exchange module, a secure communication channel between the secure portal and the user endpoint device is to be established.

I. Terminology

In the following description, certain terminology is used to describe features of the invention. For example, in certain situations, the term "logic" and "component" are representative of hardware, firmware or software that is configured to perform one or more functions. As hardware, a component (or module or logic) may include circuitry having data processing or storage functionality. Examples of such circuitry may include, but are not limited or restricted to a hardware processor (e.g., microprocessor with one or more processor cores, a digital signal processor, a programmable gate array, a microcontroller, an application specific integrated circuit "ASIC," etc.), a semiconductor memory, or combinatorial elements.

Alternatively, the component (or module or logic) may be software, such as executable code in the form of an executable application, an Application Programming Interface (API), a subroutine, a function, a procedure, an applet, a servlet, a routine, source code, object code, a shared library/dynamic load library, or one or more instructions. The software may be stored in any type of a suitable non-transitory storage medium, or transitory storage medium (e.g., electrical, optical, acoustical or other form of propagated signals such as carrier waves, infrared signals, or digital signals). Examples of non-transitory storage medium may include, but are not limited or restricted to a programmable circuit; semiconductor memory; non-persistent storage such as volatile memory (e.g., any type of random access memory "RAM"); or persistent storage such as non-volatile memory (e.g., read-only memory "ROM," power-backed RAM, flash memory, phase-change memory, etc.), a solid-state drive, hard disk drive, an optical disc drive, or a portable memory device. As firmware, the executable code may be stored in persistent storage.

The term "computing device" should be construed as electronics with the data processing capability and/or a capability of connecting to any type of network, such as a public network (e.g., Internet), a private network (e.g., a wireless data telecommunication network, a local area network "LAN", etc.), or a combination of networks. Examples of a computing device may include, but are not limited or restricted to, the following: a server, an endpoint device (e.g., a laptop, a smartphone, a tablet, a desktop computer, a netbook, a medical device, or any general-purpose or special-purpose, user-controlled electronic device); a mainframe; a router; or the like.

A "message" generally refers to information transmitted in one or more electrical signals that collectively represent electrically stored data in a prescribed format. Each message may be in the form of one or more packets, frames, HTTP-based transmissions, or any other series of bits having the prescribed format.

The term "provider" generally represents a network device, a storage device, or an endpoint device acts as a data source for the secure portal. In one non-limiting embodiment, a provider may be associated with a healthcare provider. For example, a first medical doctor may be associated with a first provider, which includes any servers, storage devices and/or endpoint devices used by the first medical doctor and a second medical doctor may be associated with a second provider, which includes any servers, storage devices and/or endpoint devices used by the second medical doctor.

The term "computerized" generally represents that any corresponding operations are conducted by hardware in combination with software and/or firmware.

The term "communicatively coupled" generally refers to any coupling that enables transmission of a message. Examples of communicatively coupling include, but are not limited or restricted to, a hardwire link or a wireless link, such as via a private or public network, or combination thereof, or via Bluetooth®.

Lastly, the terms "or" and "and/or" as used herein are to be interpreted as inclusive or meaning any one or any combination. Therefore, "A, B or C" or "A, B and/or C" mean "any of the following: A; B; C; A and B; A and C; B and C; A, B and C." An exception to this definition will occur only when a combination of elements, functions, steps or acts are in some way inherently mutually exclusive.

II. Sesame Secure Messaging System—General Architecture

Referring to FIG. 1, an exemplary block diagram of a Sesame Secure Messaging (SSM) system is shown. Herein, the Sesame Secure Messaging system comprises a secure portal 110, one or more practice management software (PMS) systems $142_1$-$142_N$ (wherein N≥1; herein, for this example, N=2) and a notification module 120, wherein the secure portal 110 and the notification module 120 interface with one or more providers $140_1$-$140_N$ (wherein N≥1; herein, for this example, N=2) and a user endpoint device 130. The secure portal 110 includes a message exchange module 111, a secure data storage 113, PMS upload module 115, and a message generation and access control logic 116. The secure portal 110 may interface (e.g., transmit or receive a message) with the user endpoint device 130 via a secure communication channel (e.g., a Secure Sockets Layer (SSL)-secured browser session). For example, as will be discussed below, the secure portal 110 may receive authentication credentials from the user endpoint device 130 over the secure communication channel 132, and upon verification of the received authentication credentials, the secure portal 110 may generate a display and provide the user endpoint device 130 with the generated display, which includes at least a representation of a secure message. For example, the display may be a webpage generated by the secure portal 110 or a graphical user interface (GUI) of a mobile application controlled by the secure portal 110.

A. Practice Management System

The practice management software (PMS) system is located at, or integrated with, each data source, for example, each healthcare provider. In one embodiment, the PMS system $142_1$ (hereinafter, "PMS $142_1$"; additionally, PMS $142_1$ will be discussed herein but the discussion applies to each PMS $142_1$-$142_N$) may be a network device that is communicatively coupled to a server, a persistent storage device and/or one or more endpoint devices of a healthcare provider such that the PMS is able to extract data from the server, the persistent storage device and/or the one or more endpoint devices. As will be discussed below, the PMS may then relay the extracted data to the PMS upload module 115 of the secure portal 110 via a secure communication channel 132. As is illustrated in FIG. 1, the PMS $142_1$ may be communicatively coupled to a data extractor $144_1$, alternatively, although not shown, it has been contemplated that the PMS $142_1$ and the data extractor $144_1$ are integrated as a single unit (e.g., within the same network device), wherein the PMS $142_1$ performs the functions of extracting data.

In one embodiment, data uploaded by the PMS upload module may include one or more of at least: personal data, imaging systems data $143_1$ (e.g., x-rays, magnetic resonance imaging (MRI) images, computerized tomography (CT) scan, etc.), uploaded notes/diagnoses, and/or calendar data (e.g., past, current and future appointments). The upload may occur automatically or via instruction from, for example, a network administrator or healthcare provider.

B. Secure Portal

The secure portal 110 may be a networking device that includes the message exchange module 111, the secure data storage 113, the PMS upload module 115 and the message generation and access control logic 116. Additionally, although not shown, the secure portal 110 may also include the notification module 120. The secure portal 110 acts as a secure messaging platform that includes logic to automatically upload data from one or more providers, parse and store the uploaded data in secure storage, automatically generate a secure message based at least in part on the uploaded data, and notify a user to which the new secure message corresponds of the presence of the new secure message in the message exchange module 111 within the secure portal 110. Significantly, the secure portal 110 stores the secure message on a message exchange module 111 within the secure portal 110 and requires the receipt of authenticating credentials from the user corresponding to the new secure message over a secure connection prior to providing the user access to the new secure message (e.g., via display of a webpage generated and controlled by the secure portal 110 or of a GUI generated and controlled by the secure portal 110).

1. PMS Upload Module

As mentioned above, the PMS upload module 115 may be communicatively coupled, or permanently or temporarily, over a secure communication channel to interface with each PMS $142_1$-$142_N$. The PMS $142_1$ may automatically receive data extracted from a server, a persistent storage device and/or one or more endpoint devices of one or more healthcare providers in a periodic or aperiodic manner (e.g., automatically receive data at a predetermined time every day or every weekend). Alternatively, or in addition, the PMS upload module 115 may provide the PMS $142_1$ with instructions regarding the extraction of data from a server, a persistent storage device and/or one or more endpoint devices of a healthcare provider. The PMS upload module 115 may upload the extracted data from the PMS $142_1$ in a periodic or aperiodic manner and subsequently store the uploaded data in the secure storage in the secure portal. In one embodiment, the PMS upload module 115 may reformat the data from a first format (e.g., as formatted by the provider $140_1$) to a second format. Alternatively, such transformation in formatting may be performed by the PMS $142_1$. Furthermore, the PMS upload module 115 may parse the extracted data and separate the data by content type (e.g., calendar events regarding scheduling, administrative information, imaging system data, diagnoses, etc.) and store in one or more databases located within the secure data storage 113 as applicable (e.g., administrative information may be stored in a separate database than imaging system data). The secure data storage 113 may include one or more of a persistent storage device integrated into the secure portal 110 network device, a persistent storage device located remotely from the secure portal 110 network device and/or cloud storage.

2. Message Generation and Access Control Logic

The message generation and access control logic 116 provides the secure portal 110 with logic for generating a new secure message, verifying authenticating credentials and providing access to one or more secure messages based on the provided authenticating credentials. Once data has been uploaded from one or more of the providers $140_1$-$104_N$, the message generation and access control logic 116 may parse the uploaded data attempting to detect one or more patterns in the uploaded data. The patterns may be derived from one or more predetermined rule sets (e.g., business rules). For example, one embodiment may include predetermined rule sets associated with the scheduling of appointments with a plurality of healthcare providers. As one non-limiting example, one rule may recite that when a first healthcare provider has previously communicated to a second healthcare provider regarding the user of the user endpoint device 130 ("the user") through the secure portal 110 (e.g., determined through packet inspection, performed by the message generation and access control logic 116, of messages exchanged between healthcare providers), a notification is to be sent to the second healthcare provider when the user has an appointment scheduled with the first healthcare provider (e.g., determined through packet inspection of uploaded data from the first healthcare provider), wherein the notification may include a reminder to store data (e.g., imaging system data) such that the data may be extracted by the PMS and uploaded by the PMS upload module 115.

Upon detecting one or more patterns, the message generation and access control logic 116 may automatically select a message template from a plurality of pre-generated message templates according to at least one of the detected one or more patterns. Upon selecting a message template, the message generation and access control logic 116 populates the selected message template with one or more elements from the parsed data stored within the secure storage 113. For example, in one embodiment, the selected message template may include a predetermined header including information corresponding to a first healthcare provider, predetermined text and a signature block of the first healthcare provider. The text of the selected message template may correspond to the detected pattern. In one embodiment, for example, parsing of uploaded data may result in the of detection a recent appointment of the user with the first healthcare provider wherein x-rays were taken and uploaded. Thereafter, the message generation and access control logic 116 may select a message template including text corresponding to an appointment in which x-rays were taken (e.g., text typically used by the first healthcare provider to recap the next steps in receiving a diagnoses regarding the x-rays). Such a message template may also include a portion for insertion of images of the x-rays that were taken. Thus, the message generation and access control logic 116 may automatically generate a new secure message by, at least, parsing uploaded data stored in the secure data storage 113, detecting one or more patterns according to a predetermined rule set, select a message template in accordance with the detected one or more patterns, and populate the selected message template with data stored in the secure data storage 113 (e.g., name and contact information of the user, diagnoses, imaging systems data, etc.).

The message generation and access control logic also includes logic for authenticating a recipient of a secure message. When a recipient attempts to retrieve a secure message using a secure communication channel, the recipient is required to provide authentication credentials, such as, for example, a username-password combination, biometric data, a combination thereof, etc. Responsive to receiving authenticating credentials, the message generation and access control logic attempts to verify the authentication credentials (by performing a comparison with stored authenticating credentials and received authenticating credentials). Upon verifying the received authenticating credentials, the message generating and access control logic provides the authenticated recipient with access to the second secure message on the secure portal.

3. Message Exchange Module

The message exchange module 111 is a platform for storing generated secure messages for the user. Upon verifying received authenticating credentials, the message generation and access control logic 116 provides the user access to one or more secure messages within the message exchange module 111. In one embodiment, the message exchange module 111 may be displayed as a listing of all read and unread secure messages on a webpage. Alternatively, the message exchange module 111 may be displayed as a listing of all read and unread secure messages through a GUI within a designated mobile application (e.g., application for a mobile device configured for network connectivity).

C. Notification Module

The notification module 120 may be a second network device, separate from the secure portal 110 network device, or as mentioned above, the notification module 120 may be logic included in the secure portal 110 network device. The notification module 120 may be communicatively coupled to the user endpoint device 130 via an unsecured communication channel (e.g., HTTPS or unsecured email such as Google Gmail™). The notification module 120 may receive a notification from the message generation and access control logic 116 that a new secure message has been generated. Responsive to receiving such a notification, the notification module 120 may generate a notification and transmit the notification to the user endpoint device 130 (e.g., the notification client 131). Importantly, the notification transmitted by the notification module 120 does not contain any sensitive information (e.g., confidential, personal, and/or medical information) but merely alerts the user of the presence of the new secure message on the secure portal 110. The notification may include a link to the secure portal 110 (e.g., a link to a webpage of the secure portal 110, or of the Sesame Secure Messaging system generally) that requires the input and verification of authentication credentials prior to displaying the secure message. Alternatively, or in addition, activation (e.g., clicking on, or selecting) the link may result in the opening of a mobile application, also requiring input and verification of authentication credentials prior to displaying the secure message.

Additionally, the notification module 120 may receive a notification from the message generation and access control logic 116 that a new secure message has been generated, wherein the a provider $140_1$-$140_N$ is to be notified. In one embodiment, as will be discussed below, the message generation and access control logic 116 may require approval of a healthcare provider associated with the provider $140_1$. Alternatively, a healthcare provider associated with the provider $140_1$ may be carbon-copied ("CC'ed") on the new secure message and receive a notification from the notification module 120 similar to the notification received by the user endpoint device 130 discussed above.

Additionally, the notification module 120 may receive a notification from the message generation and access control logic 116 that the secure portal 110 is waiting for, or expecting data to upload from a particular provider. For example, in one embodiment, a healthcare provider associated with the provider $140_1$ may have referred the user to a healthcare provider associated with the provider $140_2$. In such an situation, the secure portal 110 may be attempting to generate a new secure message for the user after an appointment of the user with the healthcare provider associated with the provider $140_1$ that includes, for example, imaging data taken by the healthcare provider associated with the provide $140_2$; however, no imaging data has been extracted by the PMS $142_2$. Thus, the notification module 120 generates a notification and transmits the notification to the provider $140_2$ to remind the healthcare provider associated with the provider $140_2$ to store the imaging data so that the imaging data may be uploaded to the secure portal 110.

III. Generation of a Secure Message

Figure 2:
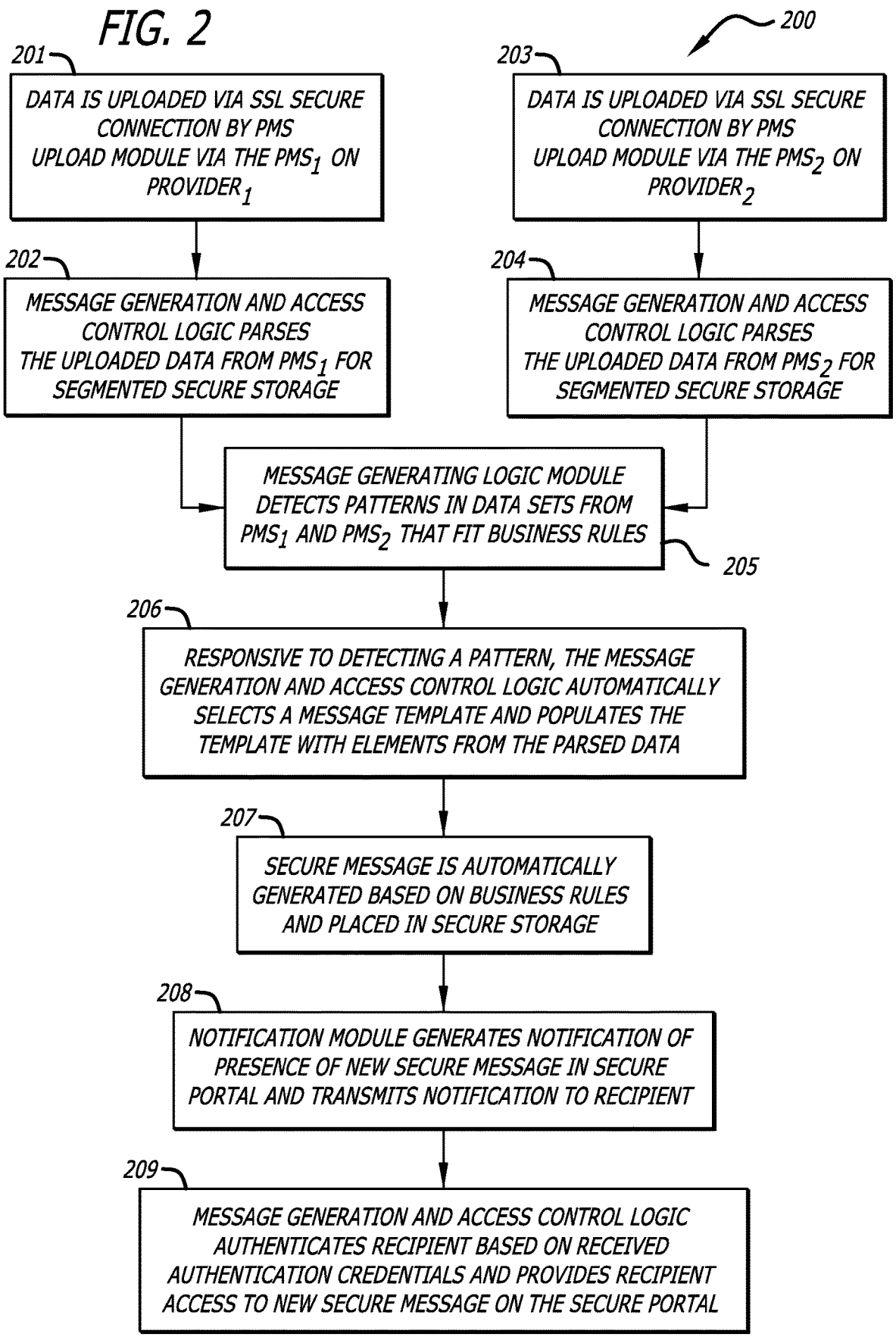
FIG. 2 is an exemplary flowchart illustrating one embodiment of a process for generating a secure message by a secure portal within the Sesame Secure Messaging system.

Referring to FIG. 2, an exemplary flowchart illustrating one embodiment of a process for generating a secure message by a secure portal within the Sesame Secure Messaging system is shown. Each block illustrated in FIG. 2 represents an operation performed in the method 200 of generating a secure message based on uploaded data from a plurality of providers. At block 201, the PMS upload module uploads data that has been extracted from one or more of a server, storage device, or endpoint device associated with provider$_1$ by the PMS$_1$ (associated with provider$_1$). The uploaded data is stored in the secure data storage of the secure portal. At block 202, the PMS upload module parses the uploaded data from PMS$_1$.

At block 203, the PMS upload module uploads data that has been extracted from one or more of a server, storage device, or endpoint device associated with provider$_2$ by the PMS$_2$ (associated with provider$_2$). The uploaded data is stored in the secure data storage of the secure portal. At block 204, the PMS upload module parses the uploaded data from PMS$_2$.

At block 205, the message generating and access control logic parses the stored data to detect patterns in the stored data based on a predetermined rule set, wherein the predetermined rule set may be based on one or more business rules. At block 206, responsive to detecting a pattern, the message generating and access control logic automatically selects a message template and populates the message template with one or more elements from the parsed data.

At block 207, the new secure message generated by populating the message template is placed in the message exchange module for secure storage. At block 208, the message generating and access control logic notifies the notification module of the presence of the new secure message for the corresponding recipient and the notification module transmits a notification to the corresponding recipient. At block 209, the message generating and access control logic receives authentication credentials and verifies the authentication credentials. Responsive to verifying the authentication credentials, the message generating and access control logic provides the recipient access to the secure message on the secure portal.

Figure 3:
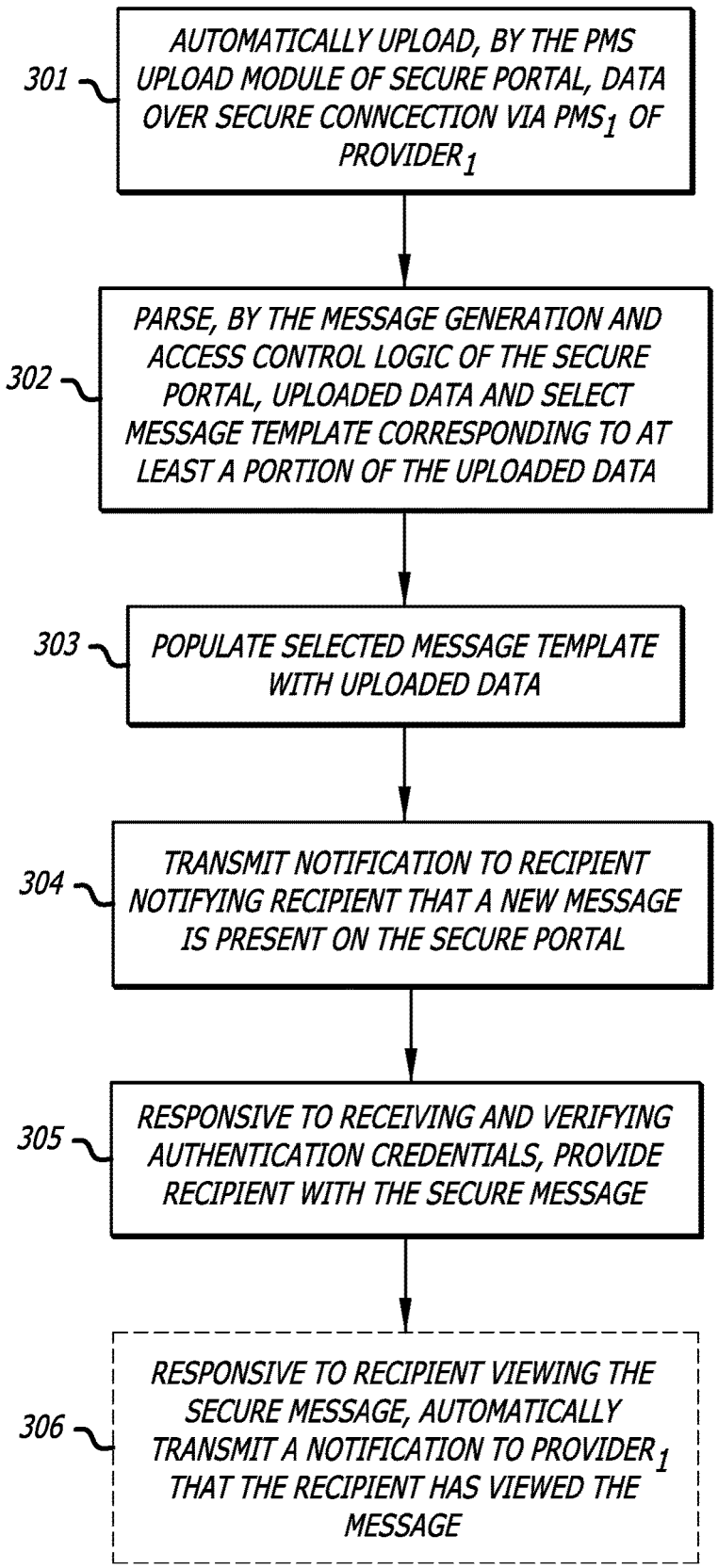
FIG. 3 is an exemplary flowchart illustrating one embodiment of a process for automatically generating a secure message by a secure portal within the Sesame Secure Messaging system using a message template determined by logic within the secure portal.

Referring to FIG. 3, an exemplary flowchart illustrating one embodiment of a process for automatically generating a secure message by a secure portal within the Sesame Secure Messaging system using a message template determined by logic within the secure portal is shown. Each block illustrated in FIG. 3 represents an operation performed in the method 300 of generating a secure message based on uploaded data from a single of provider. At block 301, the PMS upload module automatically uploads data from $PMS_1$ of $provider_1$, wherein the upload occurs over a SSL secure connection between the secure portal and $PMS_1$. At block 302, the message generating and access control logic parses the uploaded information to detect one or more patterns based on a predetermined rule set (derived from one or more business rules). Responsive to detecting a first pattern, the message generating and access control logic selects a message template.

At block 303, the message generating and access control logic populates the selected message template with at least a portion of the parsed data; therefore, generating a new secure message. For example, the portion of the parsed data that is used to populate the selected message template may include one or more of imaging systems data, administrative information (e.g., contact information, calendar events, etc.), diagnoses, lab test results, etc. The new secure message is placed in the message exchange module. At block 304, the message generating and access control logic notifies the notification module of the presence of the new secure message in the message exchange module. Upon receiving a notification of the presence of the new secure message, the notification module generates and transmits a notification to the recipient. As discussed above, the notification does not include any sensitive information but includes notice of the presence of the new secure message on the secure portal.

At block 305, responsive to receiving and verifying authentication credentials, the message generating and access control logic provides the authenticated recipient with access to the new secure message on the secure portal. For example, in one non-limiting embodiment, access may be provided by generating a webpage that includes the secure message embedded in the webpage. Alternatively, access may be provided by generating a GUI for a mobile application that is displayed on an endpoint device (e.g., a mobile telephone). At optional block 306, responsive to the recipient viewing the secure message, the message generating and access control logic notifies the notification module, which automatically generates and transmits a notification to $provider_1$ that the recipient has viewed the new secure message.

Figure 4:
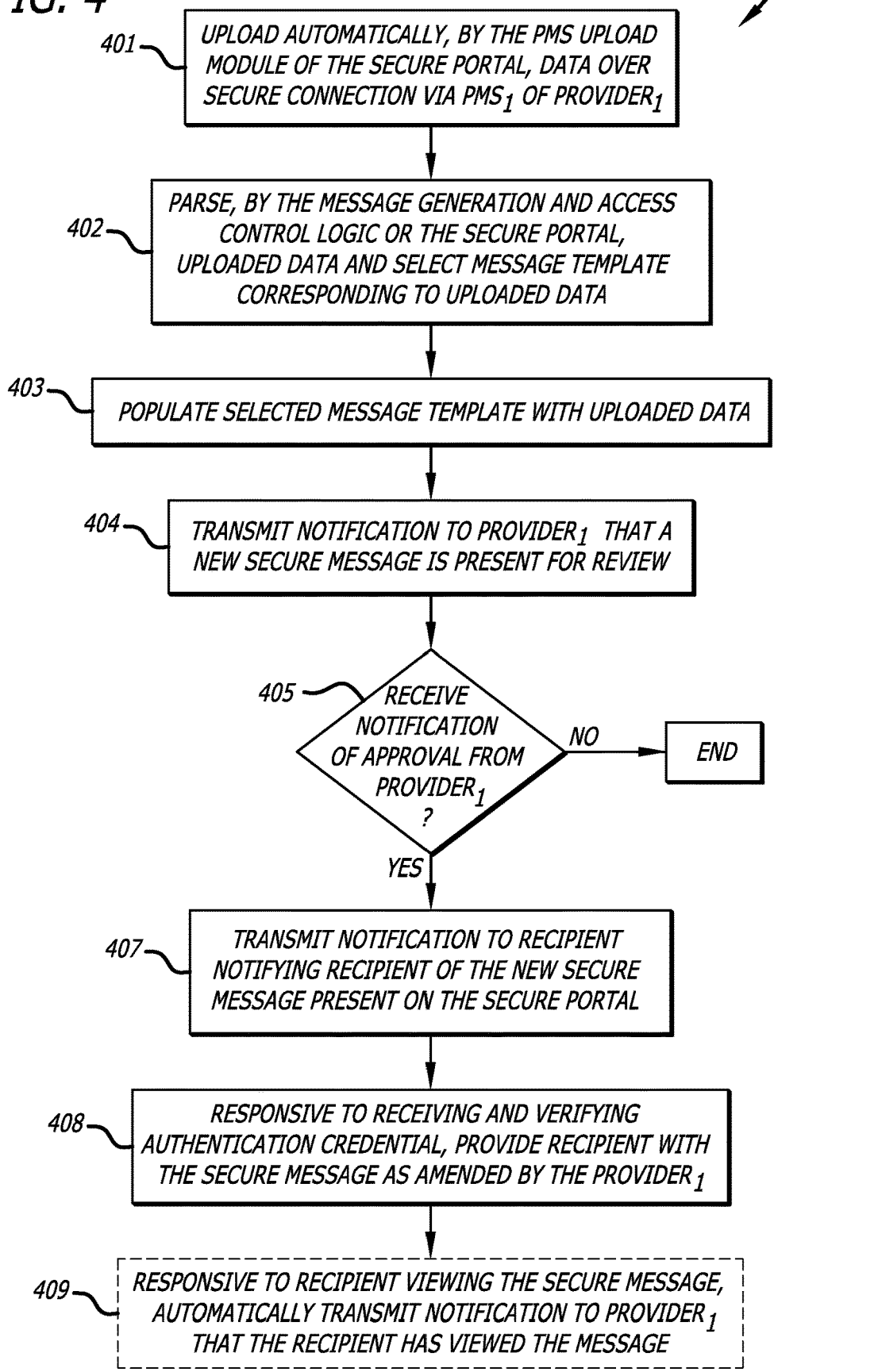
FIG. 4 is an exemplary flowchart illustrating one embodiment of a process for generating a secure message by a secure portal within the Sesame Secure Messaging system and providing the generated secure message to a provider for approval or modification.

Referring to FIG. 4, an exemplary flowchart illustrating one embodiment of a process for generating a secure message by a secure portal within the Sesame Secure Messaging system and providing the generated secure message to a provider for approval or modification is shown. Each block illustrated in FIG. 4 represents an operation performed in the method 400 of generating a secure message based on uploaded data and providing the generated secure message to a provider for approval. At block 401, the PMS upload module automatically uploads data from $PMS_1$ of $provider_1$, wherein the upload occurs over a SSL secure connection between the secure portal and $PMS_1$. At block 402, the message generating and access control logic parses the uploaded information to detect one or more patterns based on a predetermined rule set (derived from one or more business rules). Responsive to detecting a first pattern, the message generating and access control logic selects a message template. As discussed above with respect to FIG. 3, at block 403, the message generating and access control logic populates the selected message template with at least a portion of the parsed data; therefore, generating a new secure message. At block 404, the message generating and access control logic notifies the notification module of the generation of the new secure message that requires approval from a healthcare provider. In one embodiment, an automatically generated secure message may be stored in the message exchange module and the corresponding recipient notified without approval by a healthcare provider (e.g., approval for such messages was given upon using the Sesame Secure Messaging system and/or upon approval of each message template). Alternatively, as is discussed with respect to this embodiment, one or more automatically generated messages may require approval by the healthcare provider to which the secure message relates (e.g., this also provides the healthcare provider to alter the generated secure message—amend/add/remove text, attachments, etc.). Upon receiving a notification of the presence of the new secure message, the notification module generates and transmits a notification to the provider associated with the healthcare provider.

At block 405, a determination is made as to whether the healthcare provider approved the secure message (e.g., including any alterations). When the healthcare provider does not approve of the message (e.g., does not want the message to be sent) (no at block 405), the process ends and the secure message is discarded (block 406). When the healthcare provider approves the message (yes at block 405), the secure message is stored in the message exchange module and the message generating and access control logic notifies the notification module of the presence of the new secure message in the message exchange module. Upon receiving a notification of the presence of the new secure message, the notification module generates and transmits a notification to the recipient (block 407).

As discussed above with respect to FIG. 3, at block 408, responsive to receiving and verifying authentication credentials, the message generating and access control logic provides the authenticated recipient with access to the new secure message on the secure portal. At optional block 409, responsive to the recipient viewing the secure message, the message generating and access control logic notifies the notification module, which automatically generates and transmits a notification to $provider_1$ that the recipient has viewed the new secure message.

Figure 5:
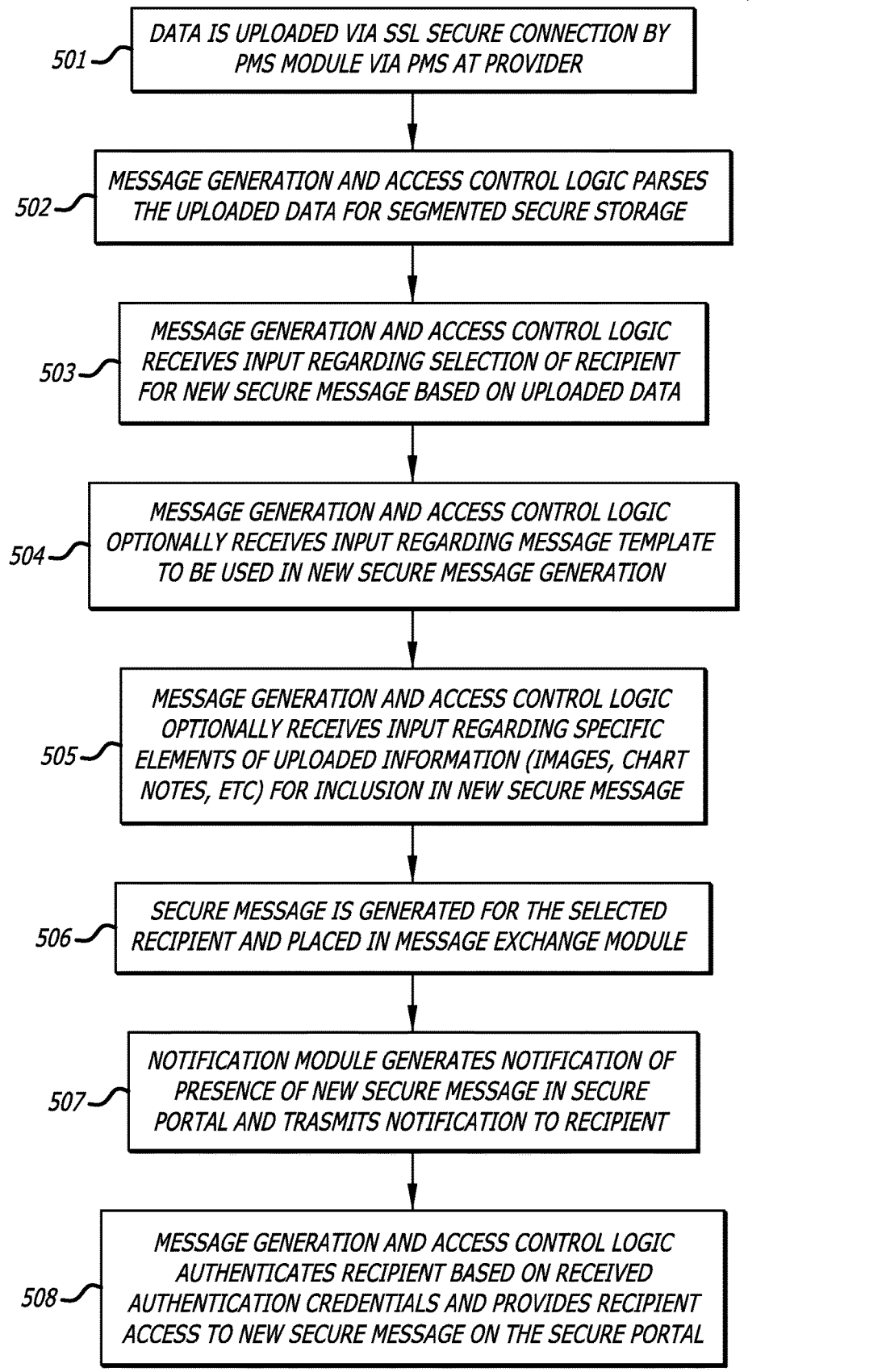
FIG. 5 is an exemplary flowchart illustrating one embodiment of a process for receiving input by the Sesame Secure Messaging system for generating a secure message using a secure portal.

Referring to FIG. 5, an exemplary flowchart illustrating one embodiment of a process for receiving input by the Sesame Secure Messaging system for generating a secure message using a secure portal is shown. Each block illustrated in FIG. 5 represents an operation performed in the method 500 of generating a secure message based on receiving input from, for example, a healthcare provider. At block 501, the PMS upload module automatically uploads data from $PMS_1$ of $provider_1$, wherein the upload occurs over a SSL secure connection between the secure portal and $PMS_1$. At block 502, the message generating and access control logic parses the uploaded information to detect one or more patterns based on a predetermined rule set (derived from one or more business rules). At block 503, the secure portal receives input pertaining to the generation of a secure message. In one embodiment, the input may correspond to the selection of a message template by a healthcare provider (e.g., or someone affiliated with the healthcare provider). At optional block 505, the secure portal may receive input that includes a selection of specific text and/or uploaded data to be included in the secure message.

At block 506, the message generation and access control logic generates the new secure message. For example, the message generation and access control logic may populate the manually selected message template with uploaded data (e.g., determined either based on parsing and pattern detection as discussed above, or by manual selection via received input) or format the data received from the healthcare provider or affiliate. At block 507, the message generating and access control logic notifies the notification module of the presence of the new secure message in the message exchange module. Upon receiving a notification of the presence of the new secure message, the notification module generates and transmits a notification to the recipient. At block 508, responsive to receiving and verifying authentication credentials, the message generating and access control logic provides the authenticated recipient with access to the new secure message on the secure portal.

Figure 6:
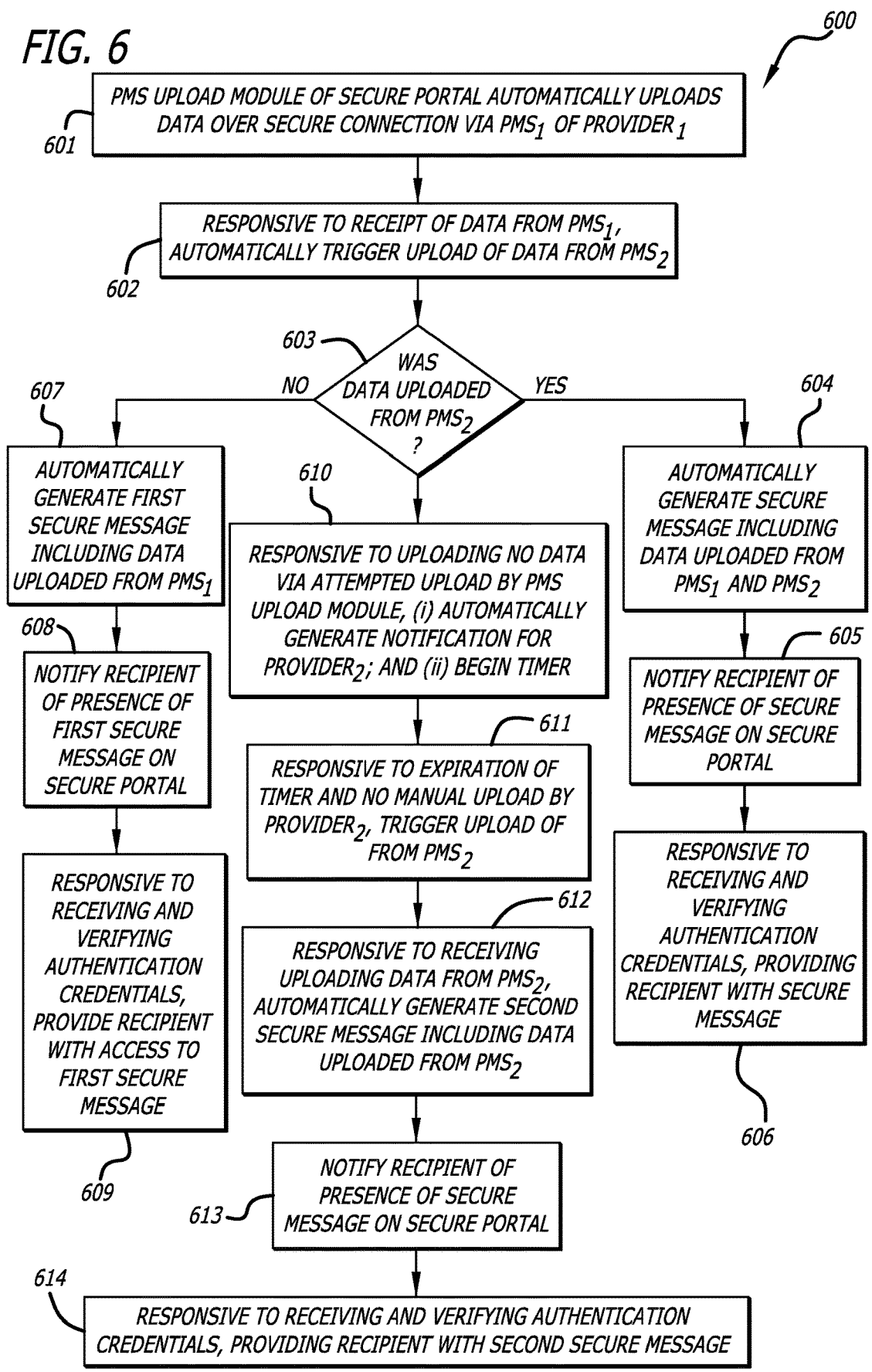
FIG. 6 is an exemplary flowchart illustrating one embodiment of a process for automatically generating a secure message by a secure portal within the Sesame Secure Messaging system and automatically triggering data upload of a second provider based on data upload from a first provider.

Referring to FIG. 6, an exemplary flowchart illustrating one embodiment of a process for automatically generating a secure message by a secure portal within the Sesame Secure Messaging system and automatically triggering data upload of a second provider based on data upload from a first provider is shown. Each block illustrated in FIG. 6 represents an operation performed in the method 600 of generating a secure message based on receiving input from a plurality of providers. At block 501, the PMS upload module automatically uploads data from $PMS_1$ of $provider_1$, wherein the upload occurs over a SSL secure connection between the secure portal and $PMS_1$. At block 602, responsive to receipt of uploaded data from $PMS_1$ of $provider_1$, the PMS upload module automatically attempts to upload data from $PMS_2$ of $provider_2$. At block 603, a determination is made as to whether data was uploaded from $PMS_2$.

When data was available for upload from $PMS_2$ (yes at block 603), the message generating and access control logic populates a selected message template with at least a portion of the parsed data; therefore, generating a new secure message (block 604). As discussed above, the message generating and access control logic may parse the uploaded data to detect one or more patterns according to a predetermined rule set based on business rules, wherein the selected message template is selected in accordance with the one or more detected patterns. The new secure message is placed in the message exchange module. At block 605, the message generating and access control logic notifies the notification module of the presence of the new secure message in the message exchange module. Upon receiving a notification of the presence of the new secure message, the notification module generates and transmits a notification to the recipient. At block 606, responsive to receiving and verifying authentication credentials, the message generating and access control logic provides the authenticated recipient with access to the new secure message on the secure portal.

When data was not available for upload from $PMS_2$ (no at block 603), two courses of action are executed concurrently (e.g., at least in part overlapping or simultaneous). In one course of action, at block 607, the message generating and access control logic parses the uploaded information to detect one or more patterns and responsive to detecting a first pattern, the message generating and access control logic selects a message template. In addition, the message generating and access control logic populates the selected message template with at least a portion of the parsed data; therefore, generating a new secure message. At block 608, the message generating and access control logic notifies the notification module of the presence of the new secure message in the message exchange module, which generates and transmits a notification to the recipient. At block 609, responsive to receiving and verifying authentication credentials, the message generating and access control logic provides the authenticated recipient with access to the new secure message on the secure portal.

In a second course of action, at block 610, responsive to uploading no data from $PMS_2$ (e.g., $PMS_2$ was unable to extract any new data from $provider_2$), the message generation and access control logic (i) notifies the notification module to generate a notification including a reminder to provide data to be uploaded to be sent to $provider_2$ (subsequently, the notification module generates and transmits such a notification to $provider_2$), and (ii) begins a timer, which represents a predetermined time period the message generation and access control logic is to wait prior to instructing the PMS upload module to attempt upload data from $PMS_2$. At block 611, responsive to the expiration of the timer and no manual upload of data by $provider_2$, an attempt to upload data from $PMS_2$ is made. At block 612, responsive to uploading data from $PMS_2$, the message generation and access control logic automatically generates a second secure message (e.g., by parsing the uploaded data to detect one or more patterns, selecting a message template based on the detected one or more patterns, and populating the selected message with at least a portion of the uploaded data). At block 613, the message generating and access control logic notifies the notification module of the presence of the second secure message in the message exchange module, which generates and transmits a notification to the recipient. At block 614, responsive to receiving and verifying authentication credentials, the message generating and access control logic provides the authenticated recipient with access to the second secure message on the secure portal.

IV. Logical Representation

Figure 7:
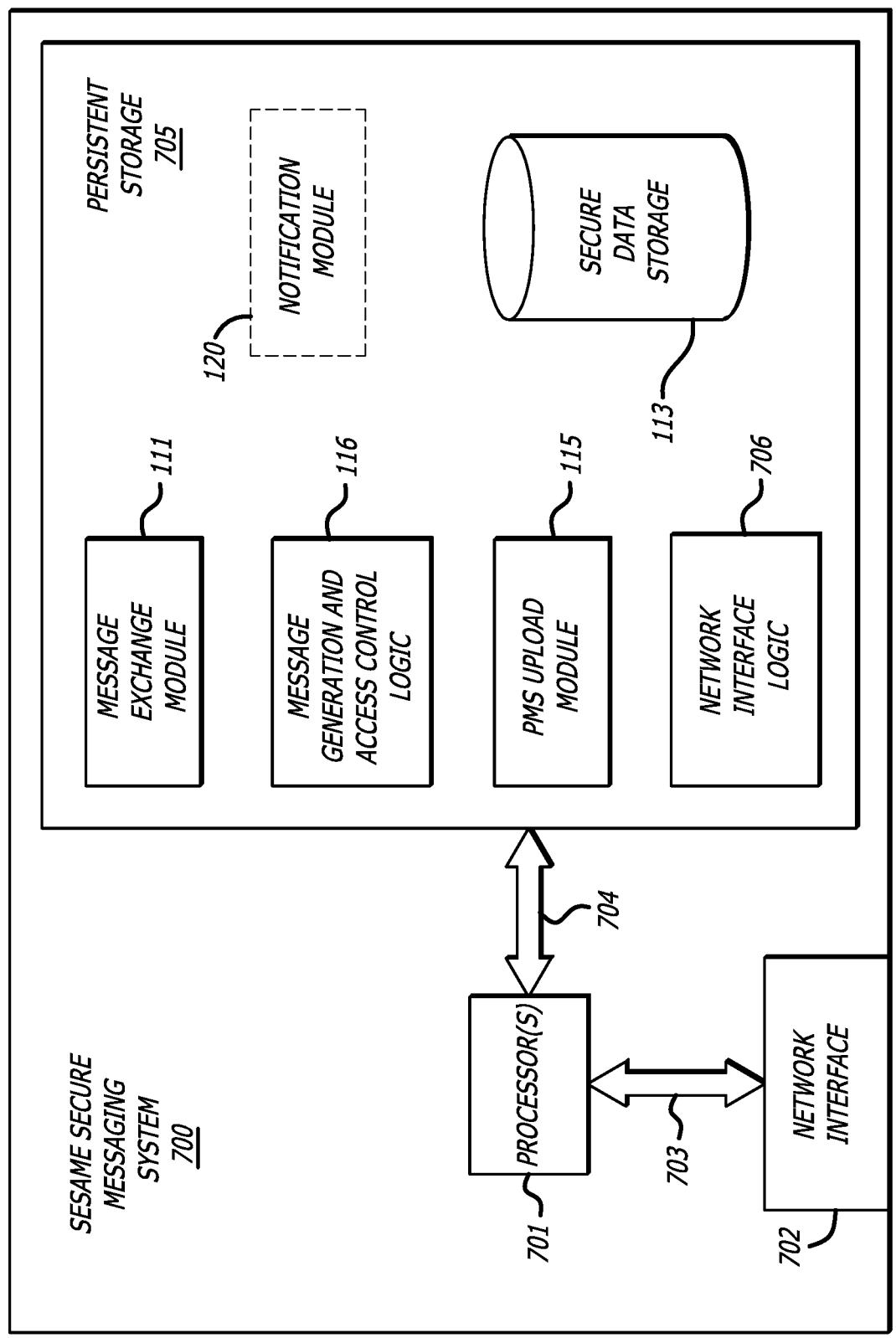
FIG. 7 is an exemplary embodiment of a logical representation of a Sesame Secure Messaging system.

Referring to FIG. 7, an exemplary embodiment of a logical representation of a Sesame Secure Messaging system is shown. The Sesame Secure Messaging system 700 includes one or more processors 701 that are coupled to network interface 702 via a first transmission medium 703. The network interface 702 and the network interface logic 706 enable communication with one or more the endpoint devices (e.g., mobile smart phone, tablet, laptop, desktop computer, etc.) via a network, such as the Internet. According to one embodiment of the disclosure, the network interface 702 may be implemented as a physical interface including one or more ports for wired connectors. Additionally, or in the alternative, the communication interface logic 706 may be implemented with one or more radio units for supporting wireless communications with other electronic devices. The network interface logic 706 may be software, hardware or a combination thereof that provides instructions for handling incoming and outgoing network traffic.

The processor(s) 701 is further coupled to persistent storage 705 via a second transmission medium 704. According to one embodiment of the disclosure, persistent storage 705 may include (a) the message exchange module 111, (b) a message generation and access control logic 116, (d) a PMS upload module 115, (e) a secure data storage 113, (f) optionally, a notification module 120, and (e) the network interface logic 706. Of course, when implemented as hardware, one or more of these logic units could be implemented separately from each other.

The notification module 120, optionally included within the same network device as the secure portal, may receive a notification from the message generation and access control logic 116 that a new secure message has been generated. Responsive to receiving such a notification, the notification module 120 may generate a notification and transmit the notification to the user endpoint device 130 (e.g., the notification client 131). The message exchange module 111 is a platform for storing generated secure messages for the user.

The message generation and access control logic 116 provides the secure portal 110 with logic for generating a new secure message, verifying authenticating credentials and providing access to one or more secure messages based on the provided authenticating credentials. The PMS upload module 115 may upload the extracted data from the PMS 142$_1$ in a periodic or aperiodic manner and subsequently store the uploaded data in the secure storage in the secure portal. Additionally, the PMS upload module 115 may parse at least a portion of the uploaded data and/or reformat at least a portion of the uploaded data. The secure data storage 113 may include one or more of a persistent storage device integrated into the secure portal 110 network device, a persistent storage device located remotely from the secure portal 110 network device and/or cloud storage.

In the foregoing description, the invention is described with reference to specific exemplary embodiments thereof. It will, however, be evident that various modifications and changes may be made thereto without departing from the broader spirit and scope of the invention as set forth in the appended claims.

What is claimed is:

1. A non-transitory storage medium having stored thereon instructions, the instructions being executable by one or more processors to perform operations comprising:
    uploading a first data from a first extractor on a first data source and a second data from a second extractor on a second data source;
    parsing the first data and the second data to detect one or more patterns within one or more of the first data or the second data;
    responsive to detecting one or more patterns, automatically selecting a message template corresponding to the one or more detected patterns;
    populating the selected message template with one or more elements from one or more of the parsed first data or the parsed second data to generate a secure message, the one or more elements corresponding to the one or more detected patterns;
    transmitting a first notification to one or more of the first data source or the second data source including a request for approval of content of the secure message; and
    responsive to receiving an approval message, storing the secure message in a secure message exchange module;
    responsive to storing the secure message in a secure message exchange module, generating a second notification that includes notice the secure message is located in the message exchange module; and
    transmitting the second notification to a recipient.

2. The storage medium of claim 1, further comprising:
    responsive to receiving authenticating credentials from the recipient, verifying the authenticating credentials; and
    providing the recipient access to the secure message over a secure communication channel.

3. The storage medium of claim 2, further comprising:
    responsive to providing the recipient access to the secure message, generating and transmitting a second notification to one or more of the first data source or the second data that access has been provided to the recipient.

4. The storage medium of claim 1, wherein the uploading of the first data and the second data is performed via a secure connection.

5. The storage medium of claim 1, wherein the uploading of the first data and the second data is performed on a periodic basis.

6. The storage medium of claim 1, wherein the one or more patterns include predetermined text having information about the recipient's personal health information.

7. The storage medium of claim 1, wherein transmission of the second notification is responsive to (1) receiving the approval, and (2) storing the storing the secure message in the secure message exchange module.

8. A method for automatically generating a secure message comprising:
    uploading a first data from a first extractor on a first data source and a second data from a second extractor on a second data source;
    parsing the first data and the second data to detect one or more patterns within one or more of the first data or the second data;
    responsive to detecting one or more patterns, automatically selecting a message template corresponding to the one or more detected patterns;
    populating the selected message template with one or more elements from one or more of the parsed first data or the parsed second data to generate a secure message, the one or more elements corresponding to the one or more detected patterns;
    transmitting a first notification to one or more of the first data source or the second data source including a request for approval of content of the secure message; and
    responsive to receiving an approval message, storing the secure message in a secure message exchange module;
    responsive to storing the secure message in a secure message exchange module, generating a second notification that includes notice the secure message is located in the message exchange module; and
    transmitting the second notification to a recipient.

9. The method of claim 8, further comprising:
    responsive to receiving authenticating credentials from the recipient, verifying the authenticating credentials; and
    providing the recipient access to the secure message over a secure communication channel.

10. The method of claim 9, further comprising:
    responsive to providing the recipient access to the secure message, generating and transmitting a third notification to one or more of the first data source or the second data that access has been provided to the recipient.

11. The method of claim 8, wherein the uploading of the first data and the second data is performed via a secure connection.

12. The method of claim 8, wherein the uploading of the first data and the second data is performed on a periodic basis.

13. A system comprising:
    one or more processors; and
    a storage medium having stored thereon instructions, the instructions being executable by one or more processors to perform operations including:
        uploading a first data from a first extractor on a first data source and a second data from a second extractor on a second data source,
        parsing the first data and the second data to detect one or more patterns within one or more of the first data or the second data,
        responsive to detecting one or more patterns, automatically selecting a message template corresponding to the one or more detected patterns,
        populating the selected message template with one or more elements from one or more of the parsed first data or the parsed second data to generate a secure message, the one or more elements corresponding to the one or more detected patterns, transmitting a first notification to one or more of the first data source or the second data source including a request for approval of content of the secure message, and responsive to receiving an approval message, storing the secure message in a secure message exchange module;

responsive to storing the secure message in a secure message exchange module, generating a second notification that includes notice the secure message is located in the message exchange module; and transmitting the second notification to a recipient.

14. The system of claim 13, further comprising:

responsive to receiving authenticating credentials from the recipient, verifying the authenticating credentials; and providing the recipient access to the secure message over a secure communication channel.

15. The system of claim 14, further comprising:

responsive to providing the recipient access to the secure message, generating and transmitting a third notification to one or more of the first data source or the second data that access has been provided to the recipient.

16. The system of claim 13, wherein the uploading of the first data and the second data is performed via a secure connection.

* * * * *